United States Patent [19]

Strom

[11] Patent Number: 5,672,724

[45] Date of Patent: Sep. 30, 1997

[54] PROCESSES FOR PREPARING RANITIDINE

[75] Inventor: Robert M. Strom, Midland, Mich.

[73] Assignee: Hoechst Marion Roussel, Inc., Cincinnati, Ohio

[21] Appl. No.: 542,408

[22] Filed: Nov. 16, 1995

Related U.S. Application Data

[63] Continuation-in-part of Ser. No. 351,985, Dec. 8, 1994, abandoned.

[51] Int. Cl.$^6$ ............................................. C07D 307/02
[52] U.S. Cl. ............................................. 549/492; 549/495
[58] Field of Search ................................ 549/492, 495

[56] References Cited

U.S. PATENT DOCUMENTS

| 4,128,658 | 12/1978 | Price et al. . |
|---|---|---|
| 4,169,855 | 10/1979 | Price et al. . |
| 4,255,440 | 3/1981 | Price et al. . |
| 4,279,819 | 7/1981 | Price et al. . |
| 4,394,516 | 7/1983 | Clitherow . |
| 4,413,135 | 11/1983 | Clitherow . |
| 4,440,938 | 4/1984 | Bradshaw . |
| 4,460,506 | 7/1984 | Bradshaw . |
| 4,497,961 | 2/1985 | Clitherow . |
| 5,030,738 | 7/1991 | Reiner . |
| 5,118,813 | 6/1992 | Reiner . |

FOREIGN PATENT DOCUMENTS

| 507.723 | 12/1981 | Spain . |
|---|---|---|
| 83-2686 | 5/1982 | Spain . |
| 540617 | 2/1985 | Spain . |
| 544063 | 6/1985 | Spain . |
| 544062 | 6/1985 | Spain . |
| 556593 | 6/1986 | Spain . |
| 550519 | 5/1987 | Spain . |

OTHER PUBLICATIONS

Moimas et al., SYNTHESES, May 1985, pp. 509–510.
Kosary, Judit et al., *Pharmazie*, 48 (1993),H. 2.
CHEMICAL ABSTRACTS, vol. 106, No. 5, 2 Feb. 1987, p. 527, col. 1, ES 544,063.
CHEMICAL ABSTRACTS, vol. 106, No. 9, 2 Mar. 1987, p. 591, col. 1, ES 544,062.

*Primary Examiner*—Amelia Owens
*Attorney, Agent, or Firm*—David M. Stemerick; Louis J. Wille

[57] ABSTRACT

The present invention relates to a novel method for preparing ranitidine and pharmaceutically acceptable salts thereof.

6 Claims, No Drawings

PROCESSES FOR PREPARING RANITIDINE

This is a continuation-in-part of application Ser. No. 08/351,985, filed Dec. 8, 1994, abandoned which is hereby incorporated by reference.

The present invention relates to a novel process for preparing ranitidine, N-[2-[[[5-(dimethylamino)methyl-2-furanyl]methyl]thio]ethyl]-N'-methyl-2-nitro-1,1-ethenediamine, and pharmaceutically acceptable salts thereof, an antagonist of the $H_2$-histamine receptor which is useful in the treatment of gastric and peptic ulcers (U.S. Pat. No. 4,128,658, Dec. 5, 1978). The process of the present invention provides a novel and efficient method for preparing ranitidine and pharmaceutically acceptable salts thereof.

SUMMARY OF THE INVENTION

The present invention provides a novel process for preparing ranitidine and pharmaceutically acceptable salts thereof, comprising:

reacting 2-nitromethylene-thiazolidine with methylamine to give a reaction mixture and then reacting the reaction mixture with an appropriate 5-[(dimethylamino)methyl]-furan derivative.

DETAILED DESCRIPTION OF THE INVENTION

As used in this application:

a) the terms "ranitidine" or "N-[2-[[[5-(dimethylamino)methyl-2-furanyl]methyl]thio]ethyl]-N'-methyl-2-nitro-1,1-ethenediamine" refer to a compound of the formula

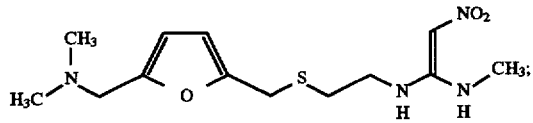

b) the term "pharmaceutically acceptable salts" refers to acid addition salts.

The expression "pharmaceutically acceptable acid addition salts" is intended to apply to any non-toxic organic or inorganic acid addition salt of ranitidine. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, and sulfonic acids such as p-toluenesulfonic acid, methanesulfonic acid and 2-hydroxyethanesulfonic acid. Such salts can exist in either a hydrated or substantially anhydrous form.

The preparation of ranitidine utilizing the economical starting material 2-nitromethylene-thiazolidine (1) is desirable. Such a process would probably proceed through N-(2-mercaptoethyl)-N'-methyl-2-nitro-1,1-ethenediamine (2). Contrary to reports in the art, N-(2-mercaptoethyl)-N'-methyl-2-nitro-1,1-ethenediamine (2) is not an isolatable solid characterized by a melting point of about 177°–180° C. (dec). In fact, compound 2 may not be isolatable. The difficulties in isolating compound 2 are explained by the equilibrium and reactions shown in Reaction Scheme A.

Reaction Scheme A

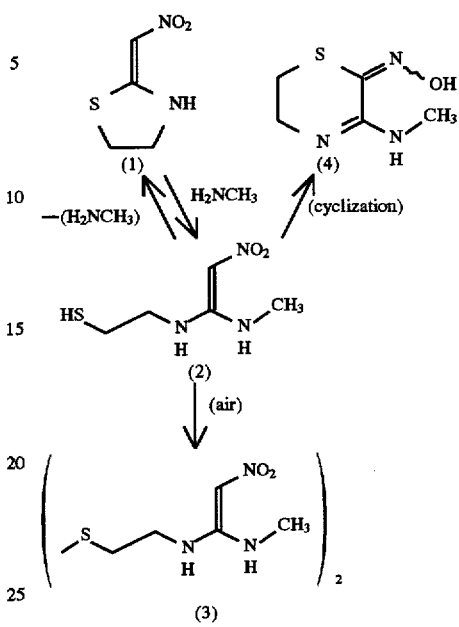

As disclosed in Reaction Scheme A, when 2-nitromethylene-thiazolidine (1) is contacted with methylamine an equilibrium is established between the addition product, N-(2-mercaptoethyl)-N'-methyl-2-nitro-1,1-ethenediamine (2) and 2-nitromethylene-thiazolidine (1). Also, as is appreciated in the art, N-(2-mercaptoethyl)-N'-methyl-2-nitro-1,1-ethenediamine (2), in the presence of a base, such as methylamine, is also in equilibrium with the mercaptide anion derived therefrom.

The equilibrium concentration of compound 2 depends on various factors, including the concentration of methylamine. The equilibrium constant for the above reaction of compound 1 with methylamine to give compound 2 is derived from the expression:

[compound 2]/[compound 1][methylamine]

wherein the terms "[compound 2]" refers to the equilibrium concentration of compound 2 in mol/L, "[compound 1]" refers to the equilibrium concentration of compound 1 in mol/L, and "[methylamine]" refers to the equilibrium concentration of methylamine in mol/L. In acetonitrile and isopropanol that equilibrium constant has a value of about 2 L/mol.

In addition to reacting by loss of methylamine to give compound 1, compound 2 can, in the presence of air or other oxidizing conditions, form the disulfide (3), N-methyl-N'-[2-[2-(N"-methyl-2-nitro-1,1-ethenediamine)ethyldisulfanyl]ethyl]-2-nitro-1,1-ethenediamine, an isolatable solid characterized by a melting point of about 177°–180° C. (dec), which was previously reported in the art to be compound 2. Even though disulfide 3 may be a useful intermediate for forming ranitidine utilizing other processes, it represents a non-productive by-product in a process which directly uses compound 2 as an intermediate.

Also, compound 2 can cyclize to form 3-methylamino-5,6-dihydro-[1,4]thiazin-2-one oxime, compound 4. In the depiction of compound 4 it is understood that the compound 3-methylamino-5,6-dihydro-[1,4]thiazin-2-one oxime can exist in a number of isomeric and tautomeric states. The formation of compound 4 is detrimental to any process which uses compound 2 because it is not in equilibrium with compound 2 and represents a non-productive by-product.

It has now been found that the direct use of N-(2-mercaptoethyl)-N'-methyl-2-nitro-1,1-ethenediamine (2) can be accomplished by processes which utilize the equilibria disclosed in Reaction Scheme A. The instant process utilizes the equilibria disclosed in Reaction Scheme A to prepare ranititdine using N-(2-mercaptoethyl)-N'-methyl-2-nitro-1,1-ethenediamine (2), without isolation, in a simple and economical one-pot process. The instant process uses N-(2-mercaptoethyl)-N'-methyl-2-nitro-1,1-ethenediamine (2) prepared from simple and readily available starting materials, 2-nitromethylene-thiazolidine (1) and methylamine. Thus, the instant invention provides a simple and economical process for preparing ranitidine.

A general synthetic procedure is set forth in Reaction Scheme 1 for preparing ranitidine from 2-nitromethylene-thiazolidine. In Reaction Scheme 1, reagents, techniques, and procedures used are well known and appreciated by one of ordinary skill in the art.

Reaction Scheme 1

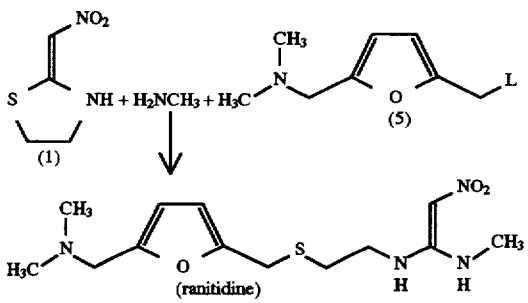

In Reaction Scheme 1, 2-nitromethylene-thiazolidine (1) is contacted with methylamine to give a reaction mixture and then the reaction mixture is contacted with an appropriate 5-[(dimethylamino)methyl]-furan derivative (5) to give ranitidine.

An appropriate 5-[(dimethylamino)methyl]-furan derivative is one in which L is a suitable leaving group. A suitable leaving groups, L, is one which can be displaced to give ranitidine. Suitable leaving groups include but are not limited to chloro, bromo, mesylate, tosylate, benzenesulfonate, and the like, with chloro being preferred. The conversion of hydroxy groups to leaving groups such as chloro, bromo, mesylate, tosylate, and benzenesulfonate is well known and appreciated in the art.

For example, 2-nitromethylene-thiazolidine is contacted with from about 1 to 20 molar equivalents of methylamine to give a reaction mixture. Initially contacting 2-nitromethylene-thiazolidine with 1 to 8 molar equivalents of methylamine being preferred and 2 to 4 molar equivalents of methylamine being more preferred. Additional methylamine may be added during the course of the reaction up to about 20 molar equivalents.

The reaction mixture is formed at a temperature of from about −20° C. to about 80° C. with temperatures of about −10° C. to about 50° C. being preferred. The reaction is carried out under an inert atmosphere, for example under nitrogen or argon.

The reaction mixture is formed in a substantially anhydrous solvent, such as acetonitrile, methanol, ethanol, propanol, butanol, isopropanol, and higher alcohols, such as pentanol, hexanol, heptanol, or octanol, with acetonitrile, methanol, ethanol, and isopropanol being preferred; acetonitrile and isopropanol being more preferred; and acetonitrile being most preferred. Optionally, the solvent may be degassed to remove oxygen.

After a time, the reaction mixture is contacted with from about 0.6 to 1.5 molar equivalents of an appropriate 5-[(dimethylamino)methyl]-furan derivative or a salt thereof. The use of from about 0.9 to 1.2 molar equivalents of an appropriate 5-[(dimethylamino)methyl]-furan derivative or a salt thereof is preferred with the use of from about 1.0 to 1.1 molar equivalents of an appropriate 5-[(dimethylamino) methyl]-furan derivative or a salt thereof being more preferred and the use of about 1.05 molar equivalents of an appropriate 5-[(dimethylamino)methyl]-furan derivative or a salt thereof being most preferred. The use of a salt of an appropriate 5-[(dimethylamino)methyl]-furan derivative is preferred.

The reaction is carried out at temperatures of from about −20° C. to about 80° C. with temperatures of from about −10° C. to about 50° C. being preferred.

When the reaction mixture is contacted with an appropriate 5-[(dimethylamino)methyl]-furan derivative or a salt thereof, the addition of an appropriate 5-[(dimethylamino) methyl]-furan derivative or a salt thereof to the reaction mixture is preferred. The reaction mixture and an appropriate 5-[(dimethylamino)methyl]-furan derivative or a salt thereof can be contacted portionwise, for example, as a single portion or a plurality of portions, or continuously.

When the addition is carried out using a plurality of portions, the amount of 5-[(dimethylamino)methyl]-furan derivative or a salt thereof added in each portion can be decreased throughout the reaction. When the addition is carried out continuously, the rate of addition of 5-[(dimethylamino)methyl]-furan derivative or a salt thereof can be decreased throughout the reaction. The addition of decreasing amounts of 5-[(dimethylamino)methyl]-furan derivative or a salt throughout the reaction is preferred.

When the addition is carried out portionwise, the temperature of the reaction can be substantially the same throughout the addition at temperatures of from about −20° C. to about 80° C. with temperatures of from about −10° C. to about 50° C. being preferred.

Alternatively, when the addition is carried out portionwise, the temperature of the reaction can be cycled such that a reaction mixture is formed at a relatively higher temperature, such as about 30° C. to about 50° C. and then the temperature of the reaction mixture is lowered to about −20° C. to about 20° C. before a portion of an appropriate 5-[(dimethylamino)methyl]-furan derivative or a salt thereof is added. After a time, the temperature can be again raised to a relatively higher temperature, such as about 30° C. to 50° C. and then the temperature of the reaction mixture is lowered to about −20° C. to about 20° C. before another portion of an appropriate 5-[(dimethylamino)methyl]-furan derivative or a salt thereof is added. This temperature cycling can be continued until the addition of an appropriate 5-[(dimethylamino)methyl]-furan derivative or a salt thereof is complete.

When the addition is carried out continuously, the temperature of the reaction can be substantially the same throughout the addition at temperatures of from about −20° C. to about 80° C. with temperatures of from about −10° C. to about 50° C. being preferred and temperatures of from about 20° C. to about 50° C. being more preferred.

Alternatively, when the addition is carried out continuously, a reaction mixture can be formed at a relatively high temperature, such as about 30° C. to about 50° C. then lowered to a temperature of about −20° C. to about 20° C. before contacting in a reaction zone, such as a continuous reactor cell, with an appropriate 5-[

(dimethylamino)methyl]-furan derivative or a salt thereof at a substantially similar lower temperature of about −20° C. to about 20° C.

The addition can be accomplished by contacting the reaction mixture with an appropriate 5-[(dimethylamino) methyl]-furan derivative or a salt thereof, either neat or as a solution or slurry in a substantially anhydrous solvent.

When a solution or slurry of an appropriate 5-[(dimethylamino)methyl]-furan derivative or a salt thereof is used, the addition can be carried out using the a different substantially anhydrous solvent or, more conveniently, the same substantially anhydrous solvent that is used to form the reaction mixture. When the addition is carried out using a solution or slurry, adjuncts may be used to increase the solubility of the appropriate 5-[(dimethylamino)methyl]-furan derivative or a salt thereof. For example, when an appropriate 5-[(dimethylamino)methyl]-furan derivative or a salt thereof is added as a solution or slurry in acetonitrile, adjuncts, such as methanesulfonic acid or hydrochloric acid, may be added.

The reaction is carried out in the presence of from about 1 to 20 molar equivalents of a suitable base. When a salt of an appropriate 5-[(dimethylamino)methyl]-furan derivative is used the reaction is carried out using from about 2 to 20 molar equivalents of a suitable base. When a salt of an appropriate 5-[(dimethylamino)methyl]-furan derivative is added in a solution or slurry containing an adjunct the reaction is carried out using from about 3 to 20 molar equivalents of a suitable base. A suitable base may be added portionwise over the course of the reaction. The use of methylamine as the suitable base is preferred, however, other bases may be used, such as triethylamine and diisopropylethylamine.

The product can be isolation by methods well known and appreciated in the art, such as extraction and evaporation. The product can be purified by methods well known and appreciated in the art, such as chromatography and recrystallization.

In an optional step, ranitidine can be contacted, as is well known in the art, with a pharmaceutically acceptable acid to form a pharmaceutically acceptable salt thereof which can be further purified by methods well known and appreciated in the art, such as recrystallization.

The foregoing process is exemplified by the procedures given below. These procedures are understood to be illustrative only and are not intended to limit the scope of the invention in any way. As used in the procedures, the following terms have the meanings indicated: "mg" refers to milligrams; "g" refers to grams; "kg" refers to kilograms; "mmol" refers to millimoles; "mol" refers to moles; "mL" refers to milliliters; "L" refers to liters; "mp" refers to melting point; "°C." refers to degrees Celsius; "dec" refers to decomposition; "M" refers to molar.

EXAMPLE 1

1.1 Synthesis of 5-[(dimethylamino)methyl]-2-(chloromethyl)-furan hydrochloride

Combine 5-[(dimethylamino)methyl]-furfuryl alcohol (25 g) and dichloromethane (100 mL). Cool to 0° C. Add dropwise, thionyl chloride (20 mL) at such a rate that the reaction does not rise above 5° C. After 0.5 hours, evaporate in vacuo to give a residue. Recrystallize the residue from ethanol to give the title compound: mp; 164°–165° C. (dec).

1.2 Synthesis of N-[2-[[[5-(dimethylamino)methyl-2-furanyl]methyl]thio]ethyl]-N'-methyl-2-nitro-1,1-ethenediamine Combine 2-nitromethylene-thiazolidine (10.0 g) and isopropanol (40 mL). Add methylamine (14.7 g). Heat to 40° C. After 5 minutes, add 5-[(dimethylamino)methyl]-2-(chloromethyl)-furan hydrochloride (13.05 g) portionwise over 1.5 hours. After 3 hours, cool to ambient temperature. Add aqueous sodium hydroxide solution (11.6 g, 50% by weight) and water (20 g). Extract repeatedly with methyl isobutyl ketone. Combine the organic layers and evaporate in vacuo to give the title compound.

EXAMPLE 2

2.1 Synthesis of 5-[(dimethylamino)methyl]-2-(chloromethyl)-furan hydrochloride

Combine 5-[(dimethylamino)methyl]-furfuryl alcohol hydrochloride (201 g, 1.05 mol) and acetonitrile (500 mL). Add dropwise, thionyl chloride (119 g, 1.0 mol) at such a rate that the temperature of the reaction is maintained at about 30° C. to 35° C. After the addition of thionyl chloride is complete, add methanesulfonic acid (144 g, 1.5 mol) while removing sulfur dioxide and acetonitrile by distillation. Stop the distillation when about 250 mL of distillate has been collected to give the title compound as a solution.

2.2 Synthesis of N-[2-[[[5-(dimethylamino)methyl-2-furanyl]methyl]thio]ethyl]-N'-methyl-2-nitro-1,1-ethenediamine Combine 2-nitromethylene-thiazolidine (146 g, 1.0 mol) and acetonitrile (250 mL). Heat to 40° C. Add methylamine (93 g, 3 mol). Cool to about 25° C. Add a solution of 5-[(dimethylamino)methyl]-2-(chloromethyl)-furan hydrochloride (1.05 mol) as obtained in Example 2.1, maintained at 50° C. to 60° C. to prevent crystallization, continuously over 5.5 hours and methylamine (5 mol) continuously over 2.5 hours. The addition trajectories of 5-[(dimethylamino) methyl]-2-(chloromethyl)-furan hydrochloride solution and methylamine are summarized in Table 1.

TABLE 1

| Time, (hr:min) | Temp. (°C.) | Methylamine (total g) | Solution from Example 2.1 (total g) |
|---|---|---|---|
| 0:00 | 24 | 93 | 0 |
| 0:25 | 27 | 119 | 97 |
| 0:55 | 27 | 149 | 203 |
| 1:27 | 26 | 181 | 303 |
| 2:35 | 27 | 248 | 448 |
| 2:52 | 25 | 248 | 467 |
| 3:40 | 27 | 248 | 517 |
| 5:30 | 26 | 248 | 579 |

When the reaction is complete, add a solution of sodium acetate (370 g) in water (780 mL). Separate the layers and extract the aqueous layer twice with acetonitrile. Combine the organic layers and evaporate in vacuo to give a residue. Partition the residue between methyl isobutyl ketone (1680 mL) and aqueous 10% potassium carbonate solution. Separate the layers and extract the aqueous layer with methyl isobutyl ketone (1680 mL). Combine the organic layers extract with water. Evaporate the organic layer in vacuo to give a residue. Recrystallize the residue from methyl isobutyl ketone to give the title compound.

EXAMPLE 3

3.1 Synthesis of 5-[(dimethylamino)methyl]-2-(chloromethyl)-furan hydrochloride

Combine 5-[(dimethylamino)methyl]-furfuryl alcohol hydrochloride (210 g, 1.1 mol) and acetonitrile (500 mL).

Cool to about 0° C. Add dropwise, thionyl chloride (113 g, 0.95 mol) over 30 minutes maintaining the temperature of the reaction below about 5° C. After the addition of thionyl chloride is complete, distill in vacuo to remove about 250 mL of distillate. Add methanesulfonic acid (144 g, 1.5 mol) to give the title compound as a solution.

3.2 Synthesis of N-[2-[[[5-(dimethylamino)methyl-2-furanyl]methyl]thio]ethyl]-N'-methyl-2-nitro-1,1-ethenediamine Combine 2-nitromethylene-thiazolidine (146 g, 1.0 mol) and acetonitrile (250 mL). Heat to 40° C. Add methylamine (90 g). After 30 minutes, cool to about −10° C. Add a solution of 5-[(dimethylamino)methyl]-2-(chloromethyl)-furan hydrochloride as obtained in Example 3.1, maintained at 50° C. to 60° C. to prevent crystallization (about 322 g of solution over 3 hours). Add methylamine (120 g). Warm to 40° C. while adding methylamine (65 g). After 30 minutes, cool to 0° C. Add the remainder of the solution of 5-[(dimethylamino)methyl]-2-(chloromethyl)-furan hydrochloride. After the addition is complete, evaporate in vacuo to give a residue. Partition the residue between methyl isobutyl ketone and aqueous 10% potassium carbonate solution. Separate the layers and extract the aqueous layer with methyl isobutyl ketone. Combine the organic layers extract with water. Evaporate the organic layer in vacuo to give a residue. Recrystallize the residue from methyl isobutyl ketone to give the title compound.

EXAMPLE 4

4.1 Synthesis of 5-[(dimethylamino)methyl]-2-(chloromethyl)-furan hydrochloride

Combine 5-[(dimethylamino)methyl]-furfuryl alcohol hydrochloride (1.72 kg, 8.97 mol) and acetonitrile (4.3 L). Cool to about 10° C. Add thionyl chloride (1.02 kg, 8.54 mol) dropwise, while maintaining the temperature of the reaction at below about 40° C. After the addition of thionyl chloride is complete, add methanesulfonic acid (1.3 kg, 13.5 mol). Distill to remove about 1.8 L of distillate to give the title compound as a solution.

4.2 Synthesis of N-[2-[[[5-(dimethylamino)methyl-2-furanyl]methyl]thio]ethyl]-N'-methyl-2-nitro-1,1-ethenediamine Combine 2-nitromethylene-thiazolidine (1.25 kg, 8.53 mol) and acetonitrile (2.15 L). Add methylamine (0.85 kg). While maintaining the temperature of the reaction at below 35° C., add a solution of 5-[(dimethylamino)methyl]-2-(chloromethyl)-furan hydrochloride as obtained in Example 4.1, maintained at 50° C. to 60° C. to prevent crystallization. During the first hour, add about half to the solution. During the second hour, add about a quarter of the solution. During the third hour, add about an eighth of the solution. During the fourth and fifth hours, add the remainder of the solution. Add methylamine during the addition of 5-[(dimethylamino)methyl]-2-(chloromethyl)-furan hydrochloride. Add methylamine (0.18 kg) at the beginning of the addition and then seven more 0.18 kg portions, one portion about every 30 minutes, during about the first 3.5 hours of the addition. When the reaction is complete, add aqueous 32% sodium acetate solution. Separate the layers and extract the aqueous layer twice with acetonitrile (3.4 L). Combine the organic layers and evaporate in vacuo to obtain a residue. Combine the residue and methyl isobutyl ketone (2.8 L) and partially evaporate in vacuo before combining with methyl isobutyl ketone (15 L). Extract with aqueous 10% potassium carbonate solution. Separate the layers and extract the aqueous layer with methyl isobutyl ketone. Combine the organic layers extract with water. Evaporate the organic layer in vacuo to give a residue. Recrystallize the residue from methyl isobutyl ketone to give the title compound.

EXAMPLE 5

5.1 Synthesis of 5-[(dimethylamino)methyl]-2-(chloromethyl)-furan hydrochloride

Combine 5-[(dimethylamino)methyl]-2-(chloromethyl)-furan hydrochloride (20 g, 0.1 mol) and acetonitrile (50 mL). Add hydrochloric acid (5.2 g, gas, 0.15 mol). Heat to 50° C. to give the title compound as a solution.

EXAMPLE 6

6.1 Synthesis of N-methyl-N'-[2-[2-(N''-methyl-2-nitro-1,1-ethenediamine)ethyldisulfanyl]ethyl]-2-nitro-1,1-ethenediamine Combine 2-nitromethylene-thiazolidine (50.0 g) and ethanolic methylamine solution (300 mL, 2/1 by weight ethanol/methylamine). Stir vigorously. Pass a stream of air (250 ml/minute) over the top of the reaction vessel. After 16 hours, add ethanol (200 mL) and methylamine (20 g). After 8 more hours, filter and rinse with cold ethanol to give the title compound: mp 177°–180° C. (dec).

What is claimed is:

1. A process for preparing ranitidine, comprising: reacting 2-nitromethylene-thiazolidine with methylamine to give a reaction mixture and then reacting the reaction mixture with an appropriate 5-[(dimethylamino)methyl]-furan derivative.

2. A process according to claim 1 wherein the appropriate 5-[(dimethylamino)methyl]-furan derivative is 5-[(dimethylamino)methyl]-2-(chloromethyl)-furan.

3. A process according to claim 1 wherein the appropriate 5-[(dimethylamino)methyl]-furan derivative is 5-[(dimethylamino)methyl]-2-(chloromethyl)-furan hydrochloride.

4. A process according to claim 1 wherein from 0.6 to 1.5 molar equivalents of an appropriate 5-[(dimethylamino)methyl]-furan derivative is used.

5. A process according to claim 1 wherein from 0.9 to 1.2 molar equivalents of an appropriate 5-[(dimethylamino)methyl]-furan derivative is used.

6. A process according to claim 1 wherein from 1.0 to 1.1 molar equivalents of an appropriate 5-[(dimethylamino)methyl]-furan derivative is used.

* * * * *